United States Patent
Buchholtz et al.

(10) Patent No.: US 8,002,718 B2
(45) Date of Patent: *Aug. 23, 2011

(54) SHOCKWAVE SYSTEM CONTROL DEPENDENT ON PATIENT'S BLOOD PRESSURE

(75) Inventors: Gerhard Buchholtz, Erlangen (DE); Jens Fehre, Hausen (DE); Bernd Granz, Oberasbach (DE); Martin Hoheisel, Erlangen (DE); Werner Kruft, Erlangen (DE); Markus Lanski, Fürth (DE); Matthias Mahler, Erlangen (DE); Christian Meinert, Marloffstein (DE); Thomas Mertelmeier, Erlangen (DE); Ralf Nanke, Neunkirchen am Brand (DE); Manfred Rattner, Grossenseebach (DE)

(73) Assignee: Siemens Aktiengesellschaft, Munich (DE)

(*) Notice: Subject to any disclaimer, the term of this patent is extended or adjusted under 35 U.S.C. 154(b) by 1080 days.

This patent is subject to a terminal disclaimer.

(21) Appl. No.: 11/479,347

(22) Filed: Jun. 30, 2006

(65) Prior Publication Data

US 2007/0016115 A1  Jan. 18, 2007

(30) Foreign Application Priority Data

Jul. 4, 2005 (DE) .................... 10 2005 031 116

(51) Int. Cl.
*A61N 5/02* (2006.01)
(52) U.S. Cl. ............... 601/4; 600/481; 600/485; 601/2; 601/3; 607/23
(58) Field of Classification Search .......... 600/427–428, 600/431, 439, 515, 519, 534, 484; 601/2–6; 128/202.13, 202.16, 328, 702, 706; 607/9, 607/17, 18–20, 23–24
See application file for complete search history.

(56) References Cited

U.S. PATENT DOCUMENTS

| | | | | |
|---|---|---|---|---|
| 3,650,277 A * | 3/1972 | Sjostrand et al. | | 607/44 |
| 3,735,756 A * | 5/1973 | Richards et al. | | 601/2 |
| 3,835,845 A * | 9/1974 | Maher | | 601/150 |
| 3,871,360 A * | 3/1975 | Van Horn et al. | | 600/484 |
| 4,031,884 A * | 6/1977 | Henzel | | 600/431 |
| 4,412,916 A * | 11/1983 | Kell | | 210/90 |
| 4,425,920 A * | 1/1984 | Bourland et al. | | 600/485 |
| 4,453,547 A * | 6/1984 | Castel et al. | | 607/46 |
| 4,651,716 A * | 3/1987 | Forester et al. | | 601/2 |
| 4,685,461 A * | 8/1987 | Forssmann et al. | | 601/4 |
| 4,745,920 A * | 5/1988 | Forssmann et al. | | 601/4 |
| 4,791,931 A * | 12/1988 | Slate | | 607/24 |
| 4,960,129 A * | 10/1990 | dePaola et al. | | 600/508 |
| 4,998,528 A * | 3/1991 | Erhardt | | 601/4 |
| 5,231,976 A * | 8/1993 | Wiksell | | 601/4 |
| 5,266,070 A * | 11/1993 | Hagiwara et al. | | 600/27 |
| 5,313,954 A * | 5/1994 | Schwarze et al. | | 600/515 |
| 5,431,621 A * | 7/1995 | Dory | | 601/2 |
| 5,466,245 A * | 11/1995 | Spinelli et al. | | 607/17 |
| 5,630,837 A * | 5/1997 | Crowley | | 601/2 |

(Continued)

FOREIGN PATENT DOCUMENTS

CN     1543909 A    11/2004

(Continued)

*Primary Examiner* — Unsu Jung

(74) *Attorney, Agent, or Firm* — Schiff Hardin LLP

(57) ABSTRACT

In a shockwave system with a shockwave source for treatment of a patient with shockwaves, a control and evaluation unit for evaluating an input signal supplied directly thereto that is correlated with a blood pressure value of the patient determined during the treatment, and controls the shockwave source dependent on the input signal.

10 Claims, 3 Drawing Sheets

U.S. PATENT DOCUMENTS

| | | | |
|---|---|---|---|
| 5,727,558 A * | 3/1998 | Hakki et al. | 600/485 |
| 5,891,181 A * | 4/1999 | Zhu | 607/44 |
| 5,957,861 A * | 9/1999 | Combs et al. | 600/547 |
| 6,141,590 A * | 10/2000 | Renirie et al. | 607/20 |
| 6,178,352 B1 * | 1/2001 | Gruzdowich et al. | 607/44 |
| 6,512,949 B1 * | 1/2003 | Combs et al. | 600/547 |
| 6,597,939 B1 * | 7/2003 | Lampotang et al. | 600/427 |
| 6,658,298 B2 * | 12/2003 | Gruzdowich et al. | 607/44 |
| 6,814,702 B2 * | 11/2004 | Redano | 600/454 |
| 6,985,774 B2 * | 1/2006 | Kieval et al. | 607/44 |
| 7,245,967 B1 * | 7/2007 | Shelchuk | 607/14 |
| 7,366,571 B2 * | 4/2008 | Armstrong | 607/45 |
| 7,403,819 B1 * | 7/2008 | Shelchuk et al. | 607/17 |
| 7,422,562 B2 * | 9/2008 | Hatib et al. | 600/485 |
| 7,452,333 B2 * | 11/2008 | Roteliuk | 600/485 |
| 7,454,245 B2 * | 11/2008 | Armstrong et al. | 607/2 |
| 7,469,697 B2 * | 12/2008 | Lee et al. | 128/200.24 |
| 7,481,772 B2 * | 1/2009 | Banet | 600/500 |
| 7,499,747 B2 * | 3/2009 | Kieval et al. | 607/9 |
| 7,561,918 B2 * | 7/2009 | Armstrong et al. | 607/39 |
| 7,575,553 B2 * | 8/2009 | Stahmann et al. | 600/528 |
| 7,610,092 B2 * | 10/2009 | Cowan et al. | 607/33 |
| 7,621,877 B2 * | 11/2009 | Schnall | 600/507 |
| 2002/0072681 A1 * | 6/2002 | Schnall | 600/507 |
| 2004/0215085 A1 * | 10/2004 | Schnall | 600/485 |

FOREIGN PATENT DOCUMENTS

DE    36 21 935 A1    1/1988

* cited by examiner

SHOCKWAVE SYSTEM CONTROL DEPENDENT ON PATIENT'S BLOOD PRESSURE

BACKGROUND OF THE INVENTION

1. Field of the Invention

The present invention concerns a shockwave system for in vivo treatment of calculi in patients.

2. Description of the Prior Art

Shockwave systems are used in medicine in order to treat people or animals as patients with ultrasonic shockwaves. The purpose of such a treatment is usually to shatter (disintegrate) a calculus located in the patient (such as, for example, a kidney or bladder stone) with the ultrasonic shockwaves focused on the calculus. Although the shockwave treatment of a patient is benign to the patient due to its non-invasive character, it is nevertheless not free of complications.

A known problem is the triggering of heart rhythm disruptions by the ultrasonic waves. The risk of such extrasystoles is reduced by temporally synchronizing the shockwave system with the ECG, thus the heart rhythm of the treated patient, to the greatest extent possible. Further problems exist when ultrasonic shockwaves impact the patient tissue surrounding the calculus. Here the danger exists of tissue injury TO the patient. The treatment of kidney stones, for example, can easily lead to damaging the kidney parenchyma, the kidney tissue that is significantly perfused with blood. The higher the blood pressure of the patient during the shockwave treatment, the higher the probability of bleeding or initiation of tears in the kidney tissue, thus a kidney hematoma.

In the general case, high blood pressure in a patient therefore represents a contraindication for a shockwave treatment. For example, kidney stone lithotripsy is no longer undertaken for a patient having a systolic blood pressure of over 160 mmHg. Today, the blood pressure of the patient is additionally normally measured or monitored during a shockwave treatment, for example with a commercially available patient monitor for monitoring blood pressure, ECG and oxygen content of the blood. It is hereby incumbent upon the doctor, for example the doctor conducting the shockwave treatment, to always observe the patient monitor and thus monitor the blood pressure of the patient. Patient monitors also exist on which a threshold for the blood pressure can be set. If the blood pressure reaches the threshold, an optical or acoustic alarm signal is triggered.

Since the doctor is primarily occupied with the shockwave treatment, for example the stone tracking and the monitoring of the degree of destruction of the calculus, the blood pressure monitoring represents an additional burden for him or her. For the patient the risk additionally exists that the doctor (due to inattention, read errors or the like) may overlook critical blood pressure values of the patient, and the patient is thus exposed to the risks of complications. The programming of the blood pressure threshold at the patient monitor can be forgotten or the warning signal can be unnoticed.

SUMMARY OF THE INVENTION

An object of the present invention is to provide a shockwave system that is improved with regard to the danger of control parameter-dependent complications for the patient.

The above object is achieved in accordance with the invention by a shockwave system having a shockwave source for treatment of a patient with shockwaves. The shockwave system has a control and evaluation unit for evaluation of an input signal. The input signal is correlated with a blood pressure value of the patient determined during the treatment. The control and evaluation unit moreover serves for control of the shockwave source dependent on the input signal.

Through the input signal that is correlated with the blood pressure value of the patient during the treatment, information about the blood pressure value of the is supplied patient directly to the shockwave system and is further processed by the control and evaluation unit. A "detour" via the doctor or treating individual, and reliance on an acoustic or optical warning signal are avoided because the reaction of the shockwave system to the blood pressure of the patient ensues automatically. A feedback of the biological parameter "blood pressure value" of the patient to the shockwave source or, respectively, to the shockwave system thus ensues automatically.

Via the control and evaluation unit, information about the blood pressure is used in order to control the shockwave source. Patient-protective measures are thus undertaken in the shockwave system, by the shockwave source, depending on the blood pressure status. For example, given blood pressure values of the patient that are critical for the treatment it is possible to emit shockwaves only with a lower shot frequency or energy level or to deactivate the shockwave source or to block triggering thereof.

The doctor is relieved of the burden of monitoring, assessing and responding to the blood pressure of the patient and thus can fully concentrate on the shockwave treatment. Critical blood pressure values of the patient can no longer be overlooked or remain unnoticed. The danger of blood pressure-dependent complications is reduced by the mandatory coupling between blood pressure value, input signal and control of the shockwave source.

The control of the shockwave source dependent on the input signal (and thus dependent on the blood pressure value of the patient) occurs automatically or in a compulsory manner, which increases the safety of the shockwave system and protects the patient. Naturally, any patient-protective measures in the shockwave system can also require the confirmation or acknowledgement by, for example, the treating doctor, which represents an additional safety measure for the patient since the doctor always retains in complete control over the shockwave system. The inventive shockwave system primarily enables inexperienced treatment providers to be unburdened from blood pressure monitoring.

As has been previously typical, the shockwave system naturally can possess an ECG trigger input, with the ECG signal being evaluated by the control and evaluation unit together with the blood pressure signal.

The correlation of input signal and blood pressure value can be done in various ways. It is only necessary that the significant information, namely information about a blood pressure value of the patient that is of interest, dangerous or decisive for the treatment, directly arrives at the shockwave system in order to be able to be evaluated there.

The input signal can thus be a "yes/no" signal dependent on the blood pressure value. In this case the switching states of the signal are, for example, "blood pressure value of the patient is critical" or "blood pressure value of the patient is non-critical", with "critical" being, for example, a blood pressure value greater than 160 mmHg. Such an input signal can be provided, for example, by a commercially-available patient monitor that has an alarm signal output, for example upon exceeding a specific blood pressure value. The input signal can arrive at the shockwave system by a hardwired, wireless, acoustic or optical transmission. The shockwave system, for example, can receive (detect) a loud acoustic warning of the patient monitor, the optical signal of a warning light or a hardwired electrical logic voltage level as the input signal.

The input signal can also be a signal that reproduces the blood pressure value, thus for example a voltage signal proportional to the blood pressure of the patient, a digital logic signal for the digitized blood pressure value of the patient in encoded form or the like. Not only pre-processed information (as above), but also the actual blood pressure value and the temporal blood pressure curve of the patient during the shockwave treatment thus can be provided to the shockwave system. It is then entirely incumbent on the shockwave system, or the control and evaluation unit thereof to not only react to two various different switch states, but also to evaluate the actual blood pressure value of the patient or curve thereof. A significantly differentiated evaluation and thus more varied reactions or strategies of the shockwave system thus are possible. The control and evaluation unit can then generate a customized control response, or select from among a number of available responses, to an optimally effective shockwave treatment with the best patient protection under the circumstances.

The shockwave system can include a threshold switch with a threshold for the blood pressure value for evaluation of the input signal by the control and evaluation unit. The control and evaluation unit thus can react to the over-run or under-run of critical blood pressure values and control the shockwave source dependent thereon, for example to block triggering thereof. A number of thresholds can be provided in order, for example, to initiate escalatory measures for rising blood pressure values, i.e. to initially successively reduce the emission of shockwaves into the patient given a rising blood pressure and to only deactivate it entirely given a further increase. The treatment thus can be continued but without maximally stressing the patient.

The threshold switch can also exhibit (embody) a hysteresis value for the blood pressure value. For example, a resonance initiated upon exceeding a threshold or the like is then cancelled only when the blood pressure value has substantially dropped again, namely below the hysteresis value (which is in turn lower than the threshold). The shockwave treatment thus is continued in a protective manner until the patient has clearly recuperated again below the threshold limit with regard to his or her blood pressure. A new increase of the blood pressure up to the limit value again thus takes a certain time. A continuous switching of responses in the case of a blood pressure value continuously fluctuating around the limit value thus is avoided.

The thresholds and hysteresis values can be adjustable. An adaptation of the thresholds or hysteresis values to specific patients, treatment providers or other environment conditions or the like is thus possible. For example, the adjustments can be patient-dependent or automatic, for example based on data of the patient file of the patient to be treated. Institutionally-set values or preferences of various treatment providers can also be taken into account here. For example, by the specification of low thresholds the shockwave system can be designed a priori in an extremely patient-protective manner, such that an inexperienced treatment provider cannot inadvertently harm a patient. For otherwise healthy patients, experienced treatment providers can increase the thresholds or restrict the responses taken by the control and evaluation unit or associate other, less drastic patient-protective measures with the thresholds.

The shockwave system can include a signaling device to indicate the blood pressure value approaching or reaching the threshold and/or the hysteresis value. For example, the doctor can thus be notified via an optical or acoustic signal that the blood pressure of the patient approaches a critical value. The possibility is thus presented to the doctor to appropriately modify the parameters of the shockwave treatment himself before the control and evaluation unit automatically does so upon the limit value being exceeded. The doctor can then possibly take into account other measures outside of influencing the shockwave source itself, such as, for example, administering a blood pressure-lowering agent to the patient.

The shockwave system can include a base apparatus having an ECG trigger input and additionally an upstream device (series connection unit; cut-in unit) that can be connected to the ECG trigger input. The upstream device has the input for the input signal that is correlated with the blood pressure value of the patient determined during the treatment. For example, already present or known conventional shockwave systems can be used in the inventive shockwave system. These already have an ECG trigger input, but no input for an input signal correlated with the blood pressure. A control and evaluation unit interacting with the input signal is not present in such conventional systems. The feed of the input signal thus occurs via the upstream device. For example, for critical blood pressure values of the patient the triggering of the shockwave in the shockwave source can the be prevented via the ECG trigger input, dependent at least on the blood pressure value of the patient.

DESCRIPTION OF THE PREFERRED EMBODIMENTS

Figure 1:
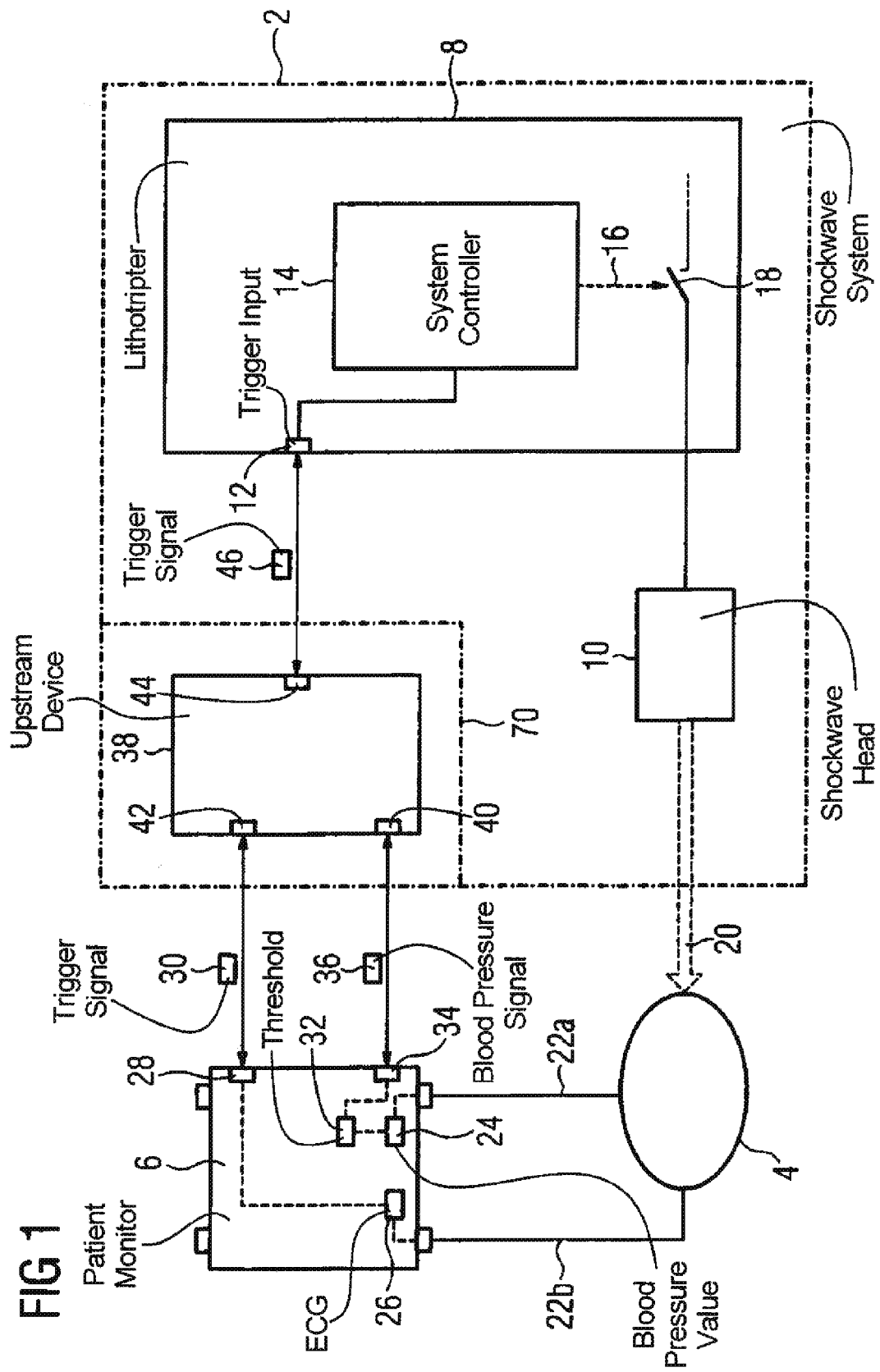
FIG. 1 shows a lithotripsy workstation with a shockwave system in a first embodiment of the invention.

FIG. 1 shows a lithotripsy workstation with a shockwave system 2, a patient 4 and a commercially-available patient monitor 6 for recording patient parameters. The shockwave system 2 includes a commercially-available lithotripter 8 with a connected shockwave head 10. The lithotripter 8 has a system controller 14 connected with an ECG trigger input 12. The system controller 14 operates (activates) a switch 18, indicated by the arrow 16. The shockwave head 10 is enabled only in the closed state of the switch 18 in order to be able to emit a ultrasonic shockwave 20 into the patient upon the occurrence of a (an additional) trigger pulse (not shown). A voltage generator feeding the shockwave head 10 via the switch 18 is used but is not shown.

The patient monitor 6 is connected to the patient 4 via measurement lines 22a and 22b. The patient monitor 6 continuously detects the patient's current blood pressure value 24 via the measurement line 22a and the ECG 26 of the patient 4 via the measurement line 22b. The patient monitor 6 evaluates the ECG 26 in a manner that need not be explained in detail such that it provides, at an ECG trigger output 28 a trigger signal 30 suitable for lithotripsy, such that the switch 18 can only be closed only at points in time when the triggering of the ultrasonic shockwave 20 is safe for the patient 4 with regard to his or her heart rhythm.

In a conventional lithotripsy system according to the prior art, the ECG trigger output 28 would be directly connected with the ECG trigger input of the lithotripter, so that by forwarding the ECG trigger signal 30 as mentioned above it is ensured that a triggering of an ultrasonic shockwave 20 ensues only in a non-critical or safe phase of the heart rhythm of the patient 4. The ECG trigger signal therefore must necessarily be present at the ECG trigger input 12 in order for the ultrasonic shockwave 20 to be triggered. In other words: the triggering of an ultrasonic shockwave 20 is suppressed by the opened switch 18 as long as no ECG trigger signal 30 is present at the ECG trigger input 12. The ECG trigger signal 30 is formed by the patient monitor 6 from the ECG 26 in a manner that need not be explained in detail.

In contrast to a conventional lithotripsy system, the shown patient monitor 6 additionally evaluates the blood pressure value 24 as well as the ECG 26. The blood pressure value 24 is compared with a threshold 32 for this purpose. The patient monitor 6 thus provides a blood pressure signal 36 at the blood pressure output 34.

Figure 2:
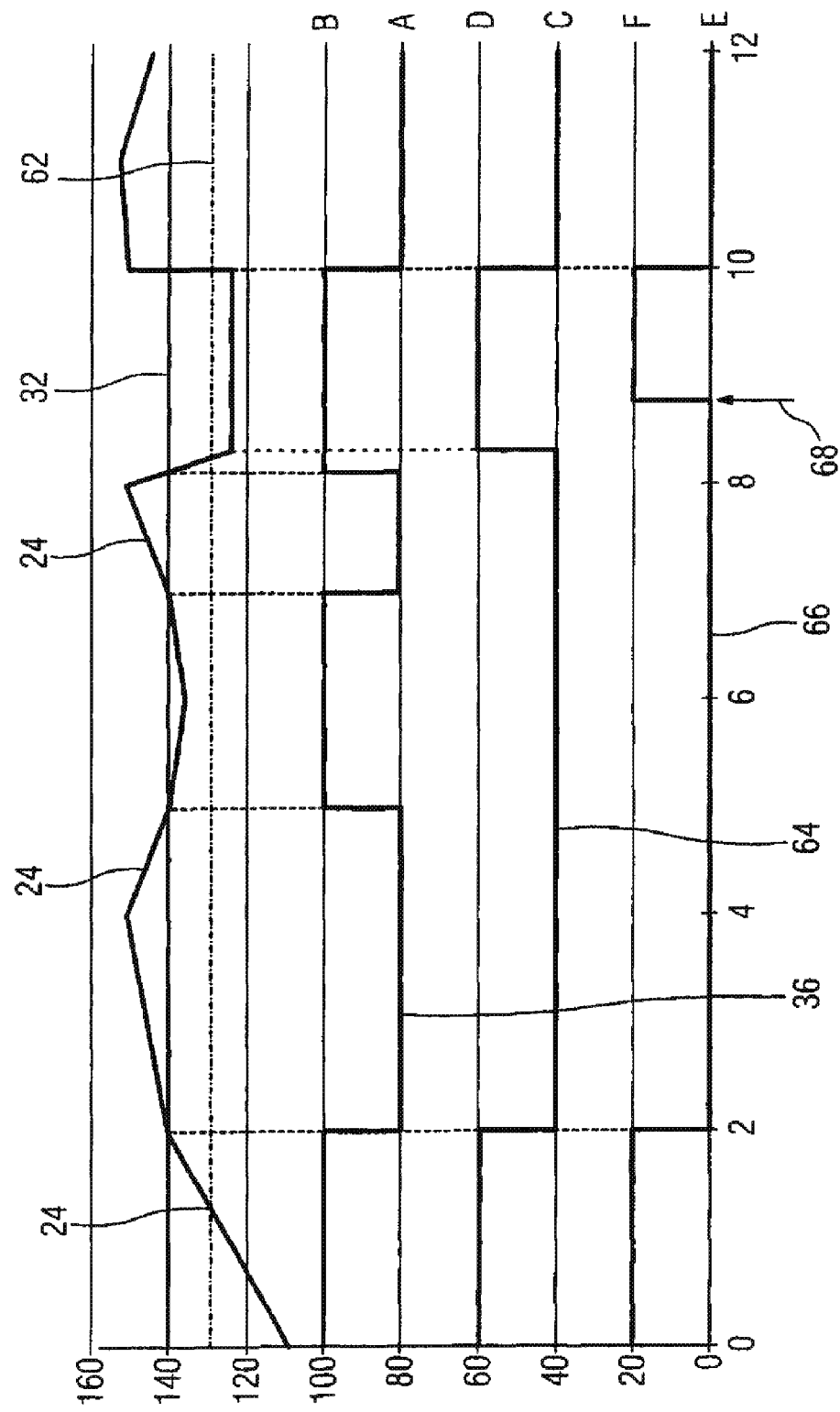
FIG. 2 shows the time curve of the blood pressure of the patient and switch signals in the shockwave system of FIG. 1.

FIG. 2 shows a time diagram of various characteristics for the lithotripsy treatment of the patient 4 from FIG. 1. The treatment time of the patient 4 is hereby plotted on the abscissa in minutes since the beginning of the treatment. The left ordinate scale, namely systolic blood pressure values in mmHg, applies for the time curve of blood pressure value 24 and threshold 32.

In the example, a threshold 32 of 140 mmHg is selected as being appropriate for the patient 4, above which threshold no treatment of the patient 4 with shockwaves 20 may occur in order to minimize the risk of a health hazard. The threshold 32, however, is arbitrarily adjustable to other values in the patient monitor 6. At the beginning of the treatment, the patient 4 exhibits a blood pressure of 110 mmHg which rises to 140 mmHg in within the first two minutes. In the time spans of 2-5 min., 7-8.2 min. and over 10 min. the blood pressure value 24 is greater than or equal to 140 mmHg, which is why no lithotripsy of the patient is permitted to occur in these time ranges.

Based on the threshold 32, the patient monitor 6 derives the blood pressure signal 36 from the blood pressure 24, the time curve of which blood pressure signal 36 is shown in FIG. 2. The blood pressure signal 36 therefore alternately occupies both switch states "A=blood pressure too high" and "B=blood pressure acceptable".

The scale of the right ordinate, namely the signal states A and B, applies for the blood pressure signal 36. The switch state B of the blood pressure signal 36 is consequently applicable only in the time spans 0-2 min., 5-7 min. and 8.2-10 min. The switch signal is found in the signal state A in the remaining time.

In contrast to the direct connection of the ECG trigger output 28 with the ECG trigger input 12 according to the prior art, the shockwave system 2 is inventively equipped with an upstream device 38 which itself has its own ECG trigger input 42 and an output 44. The upstream device 38 additionally has a blood pressure input 40. In the present case, blood pressure signal 36 and ECG trigger signal 30 are AND-linked in the upstream device 38, and a trigger signal 46 is generated from these signals. The trigger signal 46 is thus formed such that an ECG trigger signal 30 is contained in the trigger signal 46, or is switched through by the upstream device 38, only when the blood pressure signal 36 simultaneously exhibits the switch state A. A trigger signal 46 that directs the lithotripter 8 to trigger ultrasonic shockwaves 20 thus occurs only when the blood pressure 24 of the patient lies below 140 mmHg, and thus is non-critical (blood pressure signal 36 is present or is active) and an advantageous or allowed shot point is reached with regard to the ECG 26 (ECG trigger signal 30 is present or is active). The ultrasonic shot triggering is thus suppressed at such times in which the blood pressure value 24 of the patient 4 lies above the critical limit of 140 mmHg. The upstream device 38 can be configurable. In alternative embodiments, instead of the aforementioned AND-linking only the blood pressure input 40 or only the ECG trigger input 42 can be evaluated.

The upstream device 38 thus acts in the shockwave system 2 as a control and evaluation unit that evaluates the blood pressure signal 36 as an input signal. The blood pressure signal 36 is correlated with the blood pressure value 24 of the patient 4 above the threshold 32. Via the mentioned AND-linking in the upstream device 38 and the transmission of the trigger signal 46 to the lithotripter 2, the upstream device 36 thus controls the shockwave head 10 via the switch 18, dependent on the blood pressure signal 36.

Alternatively, instead of an external upstream device 38 the described function thereof can be realized internally, for example in the system controller 14.

Figure 3:
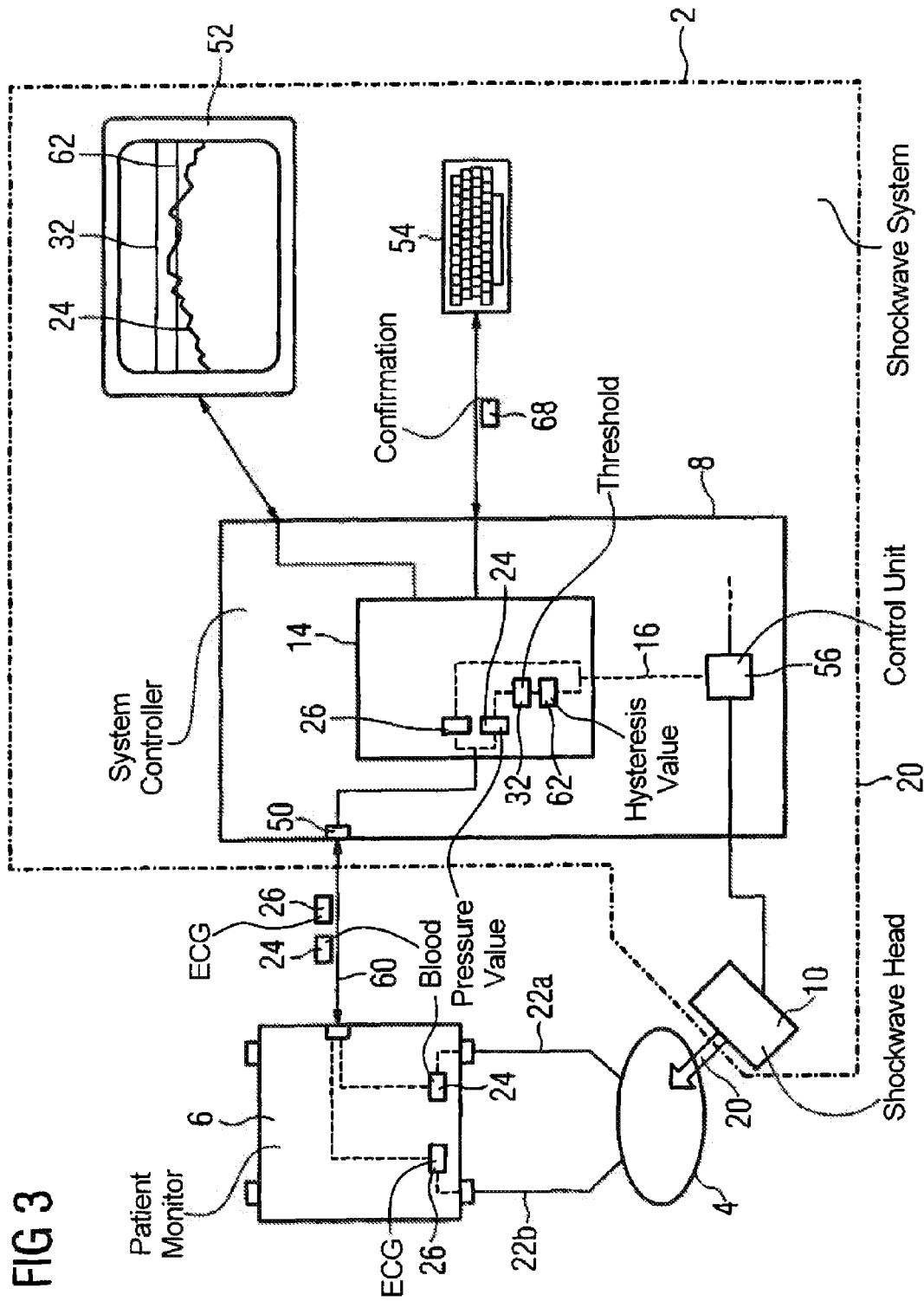
FIG. 3 shows the lithotripsy workstation of FIG. 1 with a shockwave system in an alternative embodiment of the invention.

FIG. 3 shows the lithotripsy system from FIG. 1 in an alternative embodiment with an alternative shockwave system 2. Here no external upstream device 38 is provided; the lithotripter 8 itself is therefore altered relative to the exemplary embodiment in FIG. 1. Instead of an ECG trigger input 12, the lithotripter 8 has a data interface 50 (for example an Ethernet, serial, USB, CAN, Bluetooth or parallel interface) as well as a screen 52 and a keyboard 54 connected to the system controller 14. The system controller 14 does not act (indicated by the arrow 16) on the shockwave head 10 (and therewith the ultrasonic shockwaves 20) via a mere switch 18, but rather via a control unit 56. In the control unit 56, not only can the shockwave 20 be activated and deactivated or its firing blocked, but rather operating parameters of the shockwave such as, for example, its shot frequency and energy level can be controlled.

As in FIG. 1, the patient monitor 6 records ECG 26 and blood pressure value 24 of the patient 4. In contrast to FIG. 1, however, no processing of these data occurs in the patient monitor 6. Instead the ECG 26 and the blood pressure value 24 are directly provided to the Ethernet interface 58 and transferred to the lithotripter 8 or the system controller 14 via an Ethernet cable 60 which connects this with the Ethernet interface 50.

In the system controller 14, the ECG 26 of the patient is evaluated in the known manner outlined above in order to synchronize the shockwave 20 with the heart rhythm of the patient 4. Moreover, as in FIG. 1 the blood pressure value 24 is compared with the threshold 32, but additionally with the hysteresis value 62. In the system controller 14 a blood pressure signal 64 corresponding to the blood pressure signal 36 is thus formed which in turn assumes the switch states "C—blood pressure too high" and "D—blood pressure acceptable". The threshold 32 lies unchanged at 140 mmHg and the hysteresis value at 130 mmHg.

Beginning at non-critical values of the blood pressure 24 at the point in time 0, thus at the beginning of the lithotripsy of the patient 4, the ultrasound exposure is allowed in the switch state D of the blood pressure signal 64 up to the point in time of 2 min., meaning that it ensues via the ECG 26 synchronized with the heart frequency of the patient 4. In contrast to the blood pressure signal 36, the blood pressure signal 64 only thereupon switches to the switch state D again when the blood pressure 25 has dropped below the hysteresis value 62, and not when it has fallen below the threshold 32 again. This is the case only after 8.4 min. The further time curve of the blood pressure signal 64 is again identical with that of the blood pressure signal 36.

During the entire lithotripsy treatment, a diagram according to FIG. 2 with the time curve of the blood pressure 24, the threshold 32 and the hysteresis value 62 is, for example, displayed to the doctor (not shown) on the monitor 52.

As an alternative to the embodiment just described, in the system controller 14 it can also be provided to only suppress the shot triggering of the ultrasonic shockwave 20 via the system controller 14, however not to automatically allow or, respectively, release it again. This is represented by the alternative blood pressure signal 66 generated in the system controller in FIG. 2.

Here as well the suppression of the shot triggering after 2 min. ensues via the change from the switch state F "blood pressure in order" to the switch state E "blood pressure too high", which however is only overridden again when the treating doctor confirms the resumption of the shot triggering on the keyboard 54. In FIG. 2 this ensues via the confirmation 68 after 8.8 min. which is transferred to the system controller 14 by the keyboard 54.

In addition to the cited possibilities, more complex procedures are alternatively possible in the system controller 14 with regard to the ultrasonic shockwave 20 in addition to the change between allowing and suppressing the shot triggering of the ultrasonic wave 20. For example, a number of thresholds 32 and hysteresis values 62 can be established. Given an over-run or under-run of the respective thresholds 32, the shot frequency or the energy level of the ultrasonic shockwave 20 can be successively modified dependent on the blood pressure value 24. For this purpose, the system controller activates the control unit 56 dependent on the input signals blood pressure value 24 and ECG 26. The thresholds 32 for reduction of the energy level or reduction of the shot frequency should reasonably be lower than the threshold 32 for deactivation of the ultrasonic shockwave 20. An escalatory method thus can be implemented in order to treat the patient increasingly more gently with ultrasonic shockwaves 20 given a rising blood pressure value 24, and to entirely deactivate these ultrasonic shockwaves 20 only upon reaching a critical upper limit. An escalatory regulation is generally preferable since the lithotripsy of a patient 4 would last too long if the shot triggering of the ultrasonic shockwave were blocked too often or for too long a time.

Moreover, supplementary information, for example blinking warning signals upon the blood pressure value 24 approaching a threshold 32, can be displayed to the doctor on the monitor 52. Via input on the keyboard 54, the doctor can hereupon influence the shockwave treatment or the parameters thereof according to his or her experience even before the system controller 14 automatically implements patient-protective measures, for example in the form of the reduction of the energy level of the ultrasonic shockwave 20.

Alternatively, example, the patient monitor 6 can be foregone, with the functioning thereof, for example the measurement of ECG 26 and blood pressure 24, then being integrated into the lithotripter (for example into the system controller 14) with direct connection of the sensors to the lithotripter. The evaluation still ensues as above. This is shown in FIG. 1 via the dashed line 70.

Although modifications and changes may be suggested by those skilled in the art, it is the intention of the inventors to embody within the patent warranted hereon all changes and modifications as reasonably and properly come within the scope of their contribution to the art.

We claim as our invention:

1. A shockwave system comprising:
a shockwave source that emits shockwaves adapted to interact with a patient to disintegrate a calculus in the patient during a treatment of the patient;
an ECG detector adapted to interact with the patient during said treatment to detect an ECG of the patient, and that emits an ECG signal representing the detected ECG;
a control and evaluation unit having an input connected to said ECG detector, said control and evaluation unit being configured to control administration of said shockwaves to the patient in coordination with the ECG represented in said ECG signal;
a blood pressure sensor configured to interact with the patient to directly measure blood pressure of the patient, said blood pressure sensor generating a blood pressure sensor signal representing blood pressure of the patient during said treatment; and
said control and evaluation unit comprising a further input supplied with said blood pressure sensor signal from said blood pressure sensor, and said control and evaluation unit being configured to evaluate whether said blood pressure represented in said blood pressure sensor signal satisfies a predetermined criterion, and to automatically modify the administration of shockwaves correlated with said ECG dependent on satisfaction of said criterion by said blood pressure of the patient during the treatment.

2. The shockwave system as claimed in claim 1 wherein said control and evaluation unit generates said blood pressure value-dependent signal as having only a signal state indicating said blood pressure value exceeds a critical value and a signal state indicating said blood pressure value is acceptable.

3. The shockwave system as claimed in claim 1 comprising a threshold switch connected between said blood pressure sensor and said input of said control and evaluation unit and supplying said blood pressure sensor signal to said input of said control and evaluation unit only if said blood pressure sensor signal is below a predetermined threshold.

4. The shockwave system as claimed in claim 3 wherein said threshold switch exhibits a hysteresis value for said blood pressure value.

5. The shockwave system as claimed in claim 4 wherein at least one of said threshold and said hysteresis value is adjustable.

6. The shockwave system as claimed in claim 4 comprising a signaling device that emits a humanly perceptible signal if said blood pressure value of said blood pressure sensor signal approaches or reaches at least one of said threshold and said hysteresis value.

7. The shockwave system as claimed in claim 3 wherein said threshold is adjustable.

8. The shockwave system as claimed in claim 3 comprising a signaling device that emits a humanly perceptible signal if said blood pressure value approaches or reaches said threshold.

9. The shockwave system as claimed in claim 1 wherein said shockwaves each have an amplitude and are emitted at an emission frequency, and wherein said control and evaluation unit is configured to modify at least one of said amplitude and said emission frequency dependent on whether said blood pressure satisfies said predetermined criterion.

10. The shockwave system as claimed in claim 1 wherein said control and evaluation unit is configured to discontinue administration of shockwaves, at least temporarily, dependent on whether said blood pressure satisfies said predetermined criterion.

* * * * *